(12) United States Patent
Yao et al.

(10) Patent No.: US 8,636,410 B2
(45) Date of Patent: Jan. 28, 2014

(54) MOBILE X-RAY IMAGING SYSTEM INCLUDING A STEERING MECHANISM AND A BRAKE MECHANISM

(75) Inventors: Shaohua Yao, Beijing (CN); Xueming Zeng, Beijing (CN); Lixin Gong, Beijing (CN); Weijiang Ding, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 483 days.

(21) Appl. No.: 12/901,154

(22) Filed: Oct. 8, 2010

(65) Prior Publication Data

US 2011/0096910 A1 Apr. 28, 2011

(30) Foreign Application Priority Data

Oct. 23, 2009 (CN) .......................... 2009 1 0209944

(51) Int. Cl.
*H05G 1/02* (2006.01)

(52) U.S. Cl.
USPC .......................................... 378/198; 378/197

(58) Field of Classification Search
USPC .................................. 378/197, 198
See application file for complete search history.

(56) References Cited

U.S. PATENT DOCUMENTS

| | | | | |
|---|---|---|---|---|
| 3,790,805 A | * | 2/1974 | Foderaro | ........................ 378/198 |
| 4,138,721 A | | 2/1979 | Boyd | |
| 4,223,230 A | * | 9/1980 | Waerve et al. | ................. 378/198 |
| 4,791,934 A | | 12/1988 | Brunnett | |
| 5,067,145 A | * | 11/1991 | Siczek et al. | ................... 378/198 |
| 5,351,282 A | * | 9/1994 | Kadowaki et al. | ............ 378/198 |
| 5,425,069 A | * | 6/1995 | Pellegrino et al. | ............ 378/198 |
| 5,450,466 A | | 9/1995 | Kadowaki et al. | |
| 5,503,416 A | * | 4/1996 | Aoki et al. | ................. 280/79.11 |
| 5,586,162 A | | 12/1996 | Grichnik | |
| 6,031,888 A | * | 2/2000 | Ivan et al. | ........................ 378/20 |
| 6,131,690 A | * | 10/2000 | Galando et al. | ................ 180/411 |
| 6,132,087 A | * | 10/2000 | Kusch et al. | ................... 378/197 |
| 6,200,024 B1 | | 3/2001 | Negrelli | |
| 6,212,251 B1 | * | 4/2001 | Tomura et al. | .................... 378/15 |
| 6,409,382 B1 | * | 6/2002 | Akutsu et al. | ................. 378/198 |
| 6,422,747 B2 | * | 7/2002 | Akutsu et al. | ................. 378/198 |
| 6,435,715 B1 | | 8/2002 | Betz et al. | |
| 6,609,826 B1 | * | 8/2003 | Fujii et al. | ...................... 378/198 |
| 6,763,635 B1 | * | 7/2004 | Lowman | ......................... 52/114 |
| 6,843,599 B2 | * | 1/2005 | Le et al. | ......................... 378/198 |

(Continued)

FOREIGN PATENT DOCUMENTS

| | | |
|---|---|---|
| DE | 19631246 A | 2/1998 |
| JP | 11-221206 | 8/1999 |
| JP | 2002272718 A | 9/2002 |

OTHER PUBLICATIONS

Search Report and Written Opinion from corresponding NL Application No. 2005546, Dated Mar. 5, 2012.

*Primary Examiner* — Allen C. Ho
(74) *Attorney, Agent, or Firm* — Armstrong Teasdale LLP

(57) ABSTRACT

An X-ray imaging system includes an X-ray irradiator, an X-ray receiver, a support mechanism configured to support the X-ray irradiator and X-ray receiver in opposing positions, and a flat carrier configured to support the support mechanism and including at least one wheel for movement. The X-ray imaging system also includes a handle for manual movement attached to the flat carrier car and brake means juxtaposed to the handle.

19 Claims, 2 Drawing Sheets

(56) References Cited

U.S. PATENT DOCUMENTS

| | | | |
|---|---|---|---|
| 7,016,454 B2* | 3/2006 | Warnberg | 378/9 |
| 7,322,745 B2* | 1/2008 | Agrawal et al. | 378/198 |
| 7,702,069 B2* | 4/2010 | Panesar et al. | 378/57 |
| 7,712,961 B2* | 5/2010 | Horndler et al. | 378/207 |
| 7,802,642 B2* | 9/2010 | Jensen et al. | 180/6.5 |
| 8,177,430 B2* | 5/2012 | Bouvier | 378/198 |
| 8,359,085 B2* | 1/2013 | Horndler et al. | 600/424 |
| 8,376,612 B2* | 2/2013 | Takae et al. | 378/198 |
| 8,419,276 B2* | 4/2013 | Oda et al. | 378/198 |

\* cited by examiner

MOBILE X-RAY IMAGING SYSTEM INCLUDING A STEERING MECHANISM AND A BRAKE MECHANISM

CROSS REFERENCE TO RELATED APPLICATIONS

This application claims the benefit of Chinese Patent Application No. 200910209944.9 filed Oct. 23, 2009, which is hereby incorporated by reference in its entirety.

BACKGROUND OF THE INVENTION

The present invention relates to an X-ray imaging system and more particularly to an X-ray imaging system wherein an X-ray irradiator and an X-ray receiver are supported so as to confront each other by a support mechanism installed on a flat carrier car having wheels for movement.

As a kind of an X-ray imaging system there is known a mobile X-ray imaging system. In this type of an X-ray imaging system, an X-ray irradiator and an X-ray receiver are supported in a mutually confronting manner by a support mechanism installed on a flat carrier car having moving wheels. With such an X-ray imaging system, a patient difficult to move can be subjected to radiographing at the place where the patient is (see, for example, Japanese Unexamined Patent Publication No. Hei 11 (1999)-221206 (Paragraph No. 0007-0008, FIG. 1)).

BRIEF DESCRIPTION OF THE INVENTION

Movement of this type of an X-ray imaging system is done manually. The X-ray imaging system, which is fairly heavy, is large in inertia, so when it is to be stopped urgently for some reason, a very large stopping force is considered necessary and there can be a case where the X-ray imaging system cannot be stopped by human power.

Accordingly, embodiments of the present invention provide an X-ray imaging system in which its movement can be easily stopped.

In a first aspect, there is provided an X-ray imaging system in which an X-ray irradiator and an X-ray receiver are supported so as to confront each other by a support mechanism installed on a flat carrier car having a wheel for movement, the X-ray imaging system comprising a handle for manual movement attached to the flat carrier car and brake means juxtaposed to the handle.

In a second aspect, there is provided, in combination with the first aspect, an X-ray imaging system wherein the brake means has a lever for manual operation.

In a third aspect, there is provided, in combination with the second aspect, an X-ray imaging system wherein the brake means has a brake shoe adapted to be operated by a manual operation of the lever.

In a fourth aspect, there is provided, in combination with the third aspect, an X-ray imaging system wherein the brake shoe is brought into abutment against an outer periphery of the wheel by a manual operation of the lever.

In a fifth aspect, there is provided, in combination with the fourth aspect, an X-ray imaging system wherein the brake means has a link mechanism for connection between the lever and the brake shoe.

In a sixth aspect, there is provided, in combination with any of the second to fifth aspects, an X-ray imaging system wherein the manual operation of the lever is performed by grasping the lever and the handle together.

In a seventh aspect, there is provided, in combination with the first aspect, an X-ray imaging system further comprising steering means which is operated manually by the handle.

In an eighth aspect, there is provided, in combination with the seventh aspect, an X-ray imaging system wherein the steering means changes the direction of the wheel in accordance with a manual operation of the handle.

In a ninth aspect, there is provided, in combination with the eighth aspect an X-ray imaging system wherein the steering means has a rod mechanism for connection between the handle and the wheel.

In a tenth aspect, there is provided, in combination with any of the seventh to ninth aspects, an X-ray imaging system wherein the manual operation of the handle is performed by rotating the handle.

In an eleventh aspect, there is provided, in combination with the first aspect, an X-ray imaging system wherein the wheel comprises a main wheel and an auxiliary wheel.

In a twelfth aspect, there is provided, in combination with the eleventh aspect, an X-ray imaging system wherein the brake means acts on the main wheel.

In a thirteenth aspect, there is provided, in combination with the first aspect, an X-ray imaging system wherein the support mechanism supports the X-ray irradiator and the X-ray receiver at both ends respectively of a C arm.

In a fourteenth aspect, there is provided, in combination with the thirteenth aspect, an X-ray imaging system wherein the flat carrier car supports the C arm through a support post.

In a fifteenth aspect, there is provided, in combination with the fourteenth aspect, an X-ray imaging system wherein the support post supports the C arm rotatably.

In a sixteenth aspect, there is provided, in combination with the fifteenth aspect, an X-ray imaging system wherein the support post has a power source for rotating the C arm.

In a seventeenth aspect, there is provided, in combination with the sixteenth aspect, an X-ray imaging system wherein the power source is a motor.

In an eighteenth aspect, there is provided, in combination with the first aspect, an X-ray imaging system wherein the X-ray irradiator has an X-ray tube.

In a nineteenth aspect, there is provided, in combination with the first aspect, an X-ray imaging system wherein the X-ray receiver has an image intensifier.

In a twentieth aspect, there is provided, in combination with the first aspect, an X-ray imaging system wherein the X-ray receiver has an X-ray detector panel.

According to the first aspect of the present invention, since the X-ray imaging system which supports an X-ray irradiator and an X-ray receiver in a mutually confronting manner through a support mechanism installed on a flat carrier car having a moving wheel comprises a handle for manual movement attached to the flat carrier car and brake means juxtaposed to the handle, movement of the X-ray imaging system can be stopped easily.

According to the second aspect of the present invention, since the brake means has a lever for manual operation, it is easy to perform a braking operation.

According to the third aspect of the present invention, since the brake means has a brake shoe which is operated by a manual operation of the lever, it is possible to effect braking by a manual operation.

According to the fourth aspect of the present invention, since the brake shoe is brought into abutment against an outer periphery of the wheel by a manual operation of the lever, it is possible to brake the wheel by the manual operation.

According to the fifth aspect of the present invention, since the brake means has a link mechanism for connection between the lever and the brake shoe, it is possible to transmit the operation of the lever to the brake shoe mechanically.

According to the sixth aspect of the present invention, since the manual operation of the lever is performed by grasping the lever together with the handle, it is possible to improve the operability of the lever.

According to the seventh aspect of the present invention, since the X-ray imaging system comprises steering means which is operated manually by the handle, it is possible to steer a moving direction.

According to the eighth aspect of the present invention, since the steering means changes the direction of the wheel in accordance with a manual operation of the handle, it is possible to steer the wheel.

According to the ninth aspect of the present invention, since the steering means has a rod mechanism for connection between the handle and the wheel, it is possible to transmit the operation of the handle to the wheel mechanically.

According to the tenth aspect of the present invention, since the manual operation of the handle is performed by rotating the handle, it is possible to improve the operability of the handle.

According to the eleventh aspect of the present invention, since the wheel comprises a main wheel and an auxiliary wheel, it is possible to share a load.

According to the twelfth aspect of the present invention, since the brake means acts on the main wheel, it is possible to effect braking efficiently.

According to the thirteenth aspect of the present invention, since the support mechanism supports the X-ray irradiator and the X-ray receiver at both ends respectively of a C arm, both can be confronted each other easily.

According to the fourteenth aspect of the present invention, since the flat carrier car supports the C arm through a support post, it is possible to support the C arm properly.

According to the fifteenth aspect of the present invention, since the support post supports the C arm rotatably, it is possible to change the radiographing direction.

According to the sixteenth aspect of the present invention, since the support post has a power source for rotating the C arm, human power is not required for rotating the C arm.

According to the seventeenth aspect of the present invention, since the power source is a motor, it is possible to generate power for rotation properly.

According to the eighteenth aspect of the present invention, since the X-ray irradiator has an X-ray tube, it is possible to generate X-ray properly.

According to the nineteenth aspect of the present invention, since the X-ray receiver has an image intensifier, it is possible to receive X-ray with a high sensitivity.

According to the twentieth aspect of the present invention, since the X-ray receiver has an X-ray detector panel, the X-ray receiver can be made thin.

DETAILED DESCRIPTION OF THE INVENTION

A mode for carrying out the present invention will be described below in detail with reference to the drawings. The present invention is not limited to the mode for carrying out the invention.

Figure 1:
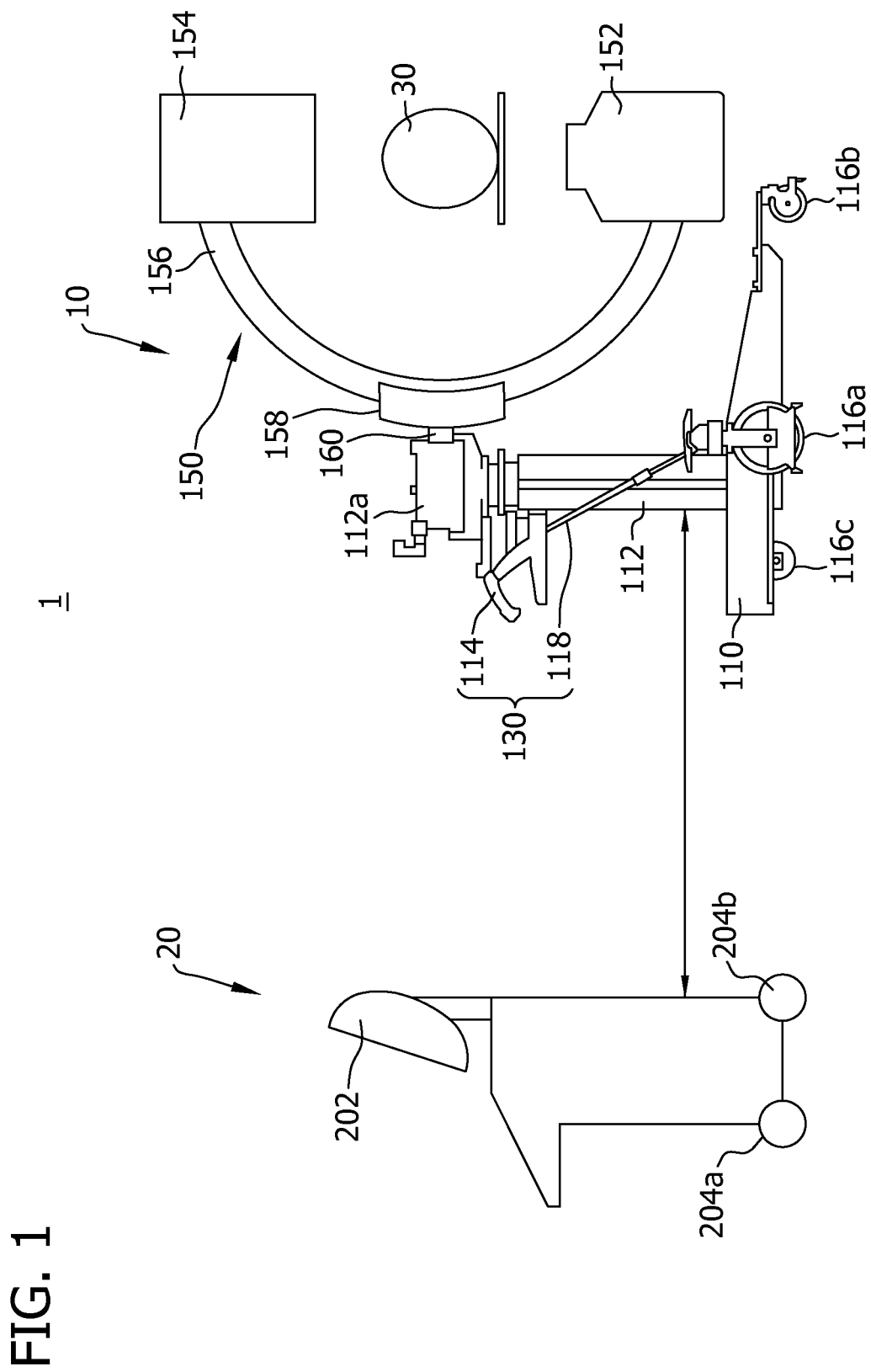
FIG. 1 is a diagram showing the configuration of an X-ray imaging system according to an embodiment of the present invention.

FIG. 1 shows schematically the configuration of an X-ray imaging system 1. The X-ray imaging system 1 is an example of the mode for carrying out the present invention. With the configuration of the X-ray imaging system 1, there is shown an example of the mode for carrying out the present invention in connection with the X-ray imaging system.

As shown in FIG. 1, the X-ray imaging system 1 has a radiographing section 10 and a control section 20. The radiographing section 10 is connected electrically to the control section 20 and performs radiographing while being controlled by the control section 20. The control section 20 serves also as an operator console. The control section 20 may be integral with the radiographing section 10. A description will be given below about an example of both being separate, the same is true of the case where both are integral.

The radiographing section 10 is of a structure wherein an X-ray irradiating/detecting apparatus 150 is attached to a support post 112 of a flat carrier car 110. The flat carrier car 110 is provided, at an upper position, with a handle 114 for manual movement and is also provided, at lower positions, with moving wheels 116a, 116b and 116c. Thus, the flat carrier car 110 can be moved manually. Of course, it can be moved by pulling.

The wheel 116a is a main wheel and the wheels 116b and 116c are auxiliary wheels. The main wheel 116a is present on each of both sides in the transverse direction (perpendicular to the paper surface) of the flat carrier car 110. The auxiliary wheels 116b and 116c are present on a front side (right side in the figure) and a rear side (left side in the figure), respectively, of the flat carrier car 110.

The handle 114 serves also as a steering handle and is connected to the main wheel 116a through a rod mechanism 118. The rod mechanism 118 converts a rotational angle of the handle 114 into a steering angle of the main wheel 116a.

Therefore, the direction of the main wheel 116a can be changed arbitrarily by operating the handle 114. On the other hand, the auxiliary wheels 116b and 116c are steering-free wheels and their directions change following movement of the flat carrier car 110.

The handle 114 and the rod mechanism 118 are an example of the steering means defined in the present invention. The mechanism comprising the handle 114 and the rod mechanism 118 will hereinafter be referred to as a steering mechanism 130.

Though not shown, the flat carrier car 110 has a brake mechanism juxtaposed to the steering mechanism 130. The brake mechanism is for braking the main wheel 116a. As to the brake mechanism, a description will be given again later.

The flat carrier car 110 is an example of the flat carrier car defined in the present invention. The support post 112 is an example of the support post defined in the present invention. The handle 114 is an example of the handle defined in the present invention. The wheels 116a, 116b and 116c are an example of the wheel defined in the present invention, of which the wheel 116a is an example of the main wheel defined in the present invention and the wheels 116b and 116c are an example of the auxiliary wheel defined in the present invention.

The X-ray irradiating/detecting apparatus 150 has a configuration such that it supports an X-ray irradiator 152 and an X-ray receiver 154 in a mutually confronting manner at both ends of a C arm 156, and the C arm is supported at an intermediate position thereof by a bracket 158. The bracket 158 supports the C arm 156 movably along the curve. The bracket 158 incorporates a drive mechanism which permits such a movement.

The bracket 158 has a horizontal rotating shaft 160, which shaft is supported by a support mechanism 112a installed at an upper end of the support post 112 of the flat carrier car 110. In the support mechanism 112a is incorporated a power source for rotating the rotating shaft 160. For example, a motor is used as the drive source.

The X-ray irradiator 152 is an example of the X-ray irradiator defined in the present invention. The X-ray receiver 154 is an example of the X-ray receiver defined in the present invention. The C arm 156 is an example of the C arm defined in the present invention. The C arm 156, bracket 158, rotating shaft 160 and support mechanism 112a are an example of the support mechanism defined in the present invention.

For radiographing, X-ray is radiated from the X-ray irradiator 152 to a patient 30 and transmitted X-ray is received by the X-ray receiver 154. The X-ray radiating direction is adjusted by changing the rotational angle of the C arm 156 and (or) the amount of movement of the C arm 156 along the curve.

The X-ray is generated from an X-ray tube incorporated in the X-ray irradiator 152. The transmitted X-ray is received by an image intensifier incorporated in the X-ray receiver 154. For receiving the X-ray there may be used an X-ray detector panel instead of the image intensifier. The X-ray detector panel is constituted by a semiconductor substrate having a two-dimensional array of X-ray receiving elements.

An X-ray reception signal from the X-ray receiver 154 is transmitted to the control section 20. On the basis of the X-ray reception signal, the control section 20 produces a radioscopic image. The radioscopic image is displayed on a display 202. The control section 20 also has moving wheels 204a and 204b and thus can be moved manually.

Figure 2:
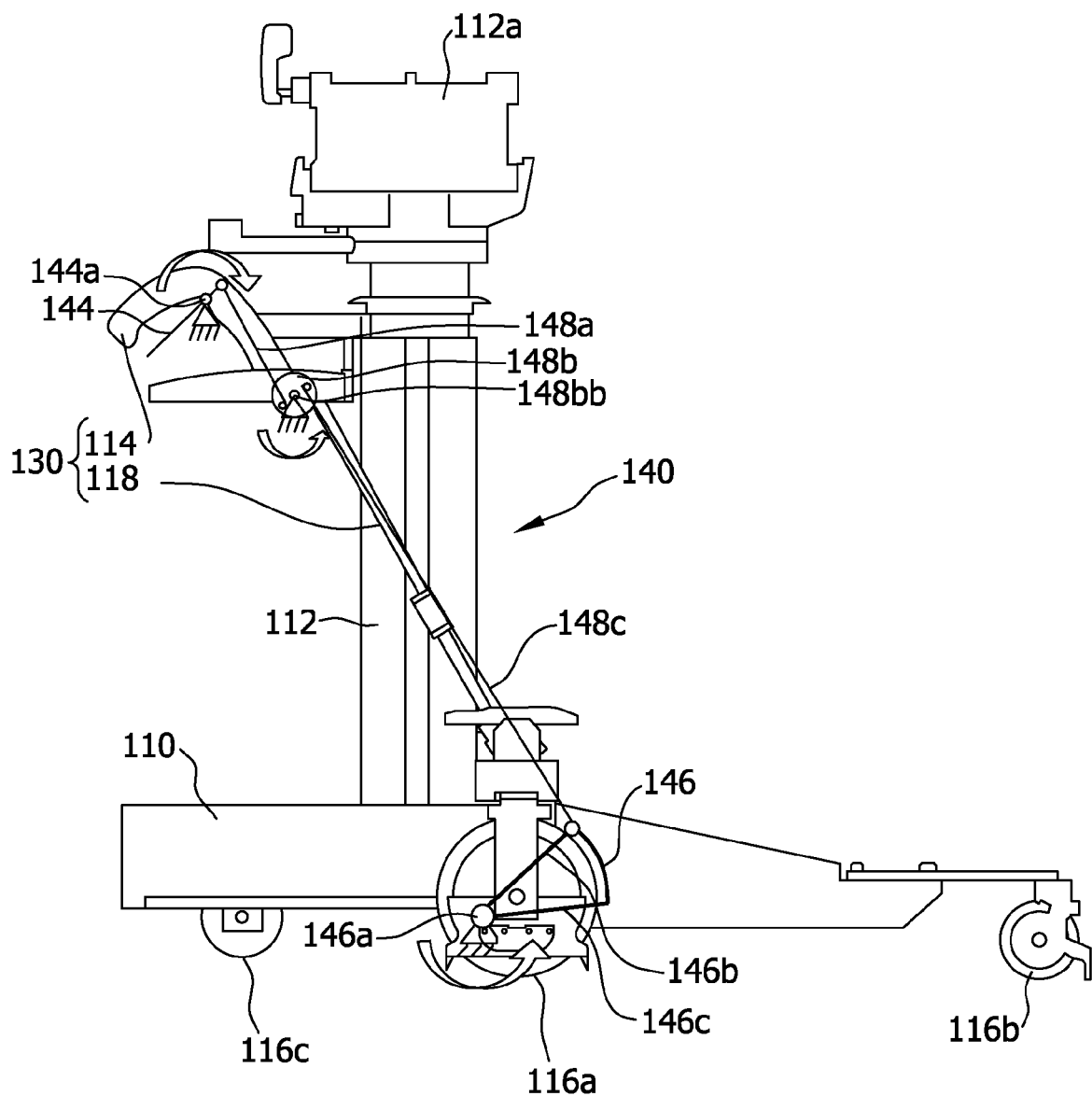
FIG. 2 is a diagram showing the configuration of a flat carrier car.

FIG. 2 shows schematically the configuration of the flat carrier car 110 equipped with a brake mechanism. As shown in FIG. 2, a brake mechanism 140 is juxtaposed to the steering mechanism 130. The brake mechanism 140 has a lever 144 for manual operation, a brake shoe 146 for braking and three links 148a, 148b and 148c for connection between the lever and the brake shoe.

The lever 144 is an example of the lever defined in the present invention. The brake shoe 146 is an example of the brake shoe defined in the present invention. The links 148a, 148b and 148c are an example of the link mechanism defined in the present invention.

The lever 144 is provided under the handle 114 so that it can be grasped together with the handle 114. A fulcrum 144a of the lever 144 is positioned near a base portion of the handle 114.

The brake shoe 146 is an arcuate member which is curved along an outer periphery of each main wheel 116a. The brake shoe 146 is supported at both ends thereof by two links 146b and 146c which are swingable about a fulcrum 146a, and is opposed to the outer periphery of the main wheel 116a without contact with the main wheel outer periphery. The fulcrum 146a of the links 146b and 146c is eccentric to an axle of the main wheel 116a. The direction of eccentricity is opposite to the brake shoe 146.

Of the three links 148a, 148b and 148c, the link 148b is a disc-like link having a fulcrum 148bb. With a spring (not shown), a reaction force which resists a counterclockwise rotation in the figure is imparted to the link 148b.

The disc-like link 148b is connected on its left end side in the figure to an operating end of the lever 144 through the link 148a and is connected on its right end side in the figure to one end of the link 146b of the brake shoe 146 through the link 148c. The connections are all joints.

In the brake mechanism 140 described above, when the lever 144 is grasped tightly together with the handle 114, the lever 144 rotates clockwise in the figure as indicated with an arrow, causing the link 148b to rotate counterclockwise in the figure through the link 148a as indicated with an arrow.

This rotation is transmitted to the link 146b through the link 148c, causing the link 146b to rotate counterclockwise in the figure as indicated with an arrow and thereby bringing the brake shoe 146 into contact with the outer periphery of the main wheel 116a. As a result, a braking force induced by a frictional force of the brake shoe 146 acts on the main wheel 116a.

Thus, since the main wheel 116a can be braked by a manual operation of the lever 144, movement of the radiographing section 10 can be stopped easily and safely even if the radiographing section is fairly heavy.

What is claimed is:

1. An X-ray imaging system comprising:
    an X-ray irradiator;
    an X-ray receiver;
    a support mechanism configured to support the X-ray irradiator and the X-ray receiver in opposing positions;
    a flat carrier car configured to support the support mechanism and comprising at least one wheel for movement;
    a handle for manual movement attached to the flat carrier car; and
    brake means juxtaposed to the handle, wherein the brake means comprises a lever for manual operation.

2. An X-ray imaging system according to claim 1, wherein the brake means further comprises a brake shoe adapted to be operated by the manual operation of the lever.

3. An X-ray imaging system according to claim 2, wherein the brake shoe is brought into abutment against an outer periphery of the at least one wheel by the manual operation of the lever.

4. An X-ray imaging system according to claim 3, wherein the brake means further comprises a link mechanism for connection between the lever and the brake shoe.

5. An X-ray imaging system according to claim 1, wherein the manual operation of the lever is performed by grasping the lever together with the handle.

6. An X-ray imaging system according to claim 1, further comprising steering means configured to be manually operated by the handle.

7. An X-ray imaging system according to claim 6, wherein the steering means is configured to change a direction of the at least one wheel in accordance with a manual operation of the handle.

8. An X-ray imaging system according to claim 7, wherein the steering means comprises a rod mechanism for connection between the handle and the at least one wheel.

9. An X-ray imaging system according to claim 6, wherein the manual operation of the handle is performed by rotating the handle.

10. An X-ray imaging system according to claim 1, wherein the at least one wheel comprises a main wheel and an auxiliary wheel.

11. An X-ray imaging system according to claim 10, wherein the brake means acts on the main wheel.

12. An X-ray imaging system according to claim 1, wherein the support mechanism comprises a C arm comprising a first end and a second end, the C arm configured to support the X-ray irradiator at the first end and to support the X-ray receiver at the second end.

13. An X-ray imaging system according to claim 12, wherein the flat carrier car comprises a support post and is configured to support the C arm through the support post.

14. An X-ray imaging system according to claim 13, wherein the support post is configured to rotatably support the C arm.

15. An X-ray imaging system according to claim 14, wherein the support post comprises a power source configured to rotate the C arm.

16. An X-ray imaging system according to claim 15, wherein the power source comprises a motor.

17. An X-ray imaging system according to claim 1, wherein the X-ray irradiator comprises an X-ray tube.

18. An X-ray imaging system according to claim 1, wherein the X-ray receiver comprises an image intensifier.

19. An X-ray imaging system according to claim 1, wherein the X-ray receiver comprises an X-ray detector panel.

* * * * *